United States Patent [19]
Allen

[11] Patent Number: 4,809,860
[45] Date of Patent: Mar. 7, 1989

[54] ASPIRATION CONTAINER ASSEMBLY FOR COLLECTING FOLLICULAR FLUIDS

[75] Inventor: Thomas C. Allen, Summerville, S.C.
[73] Assignee: Mark L. Anderson, Elmwood, Wis.
[21] Appl. No.: 129,237
[22] Filed: Dec. 7, 1987
[51] Int. Cl.[4] .............................................. B65D 1/24
[52] U.S. Cl. ................................... 220/20.5; 220/21; 220/22; 604/319
[58] Field of Search ............... 220/21, 20, 20.5, 22, 220/23.2, 23.83, 367, 82 R; 604/19, 82, 89; 206/219

[56] References Cited
U.S. PATENT DOCUMENTS

| | | | |
|---|---|---|---|
| 3,727,788 | 4/1973 | Holbrook | 220/367 |
| 3,855,997 | 12/1974 | Sauer | 604/319 |
| 4,000,829 | 1/1977 | Johnson, Jr. et al. | 220/367 |
| 4,387,998 | 6/1983 | Szigeti | 220/20.5 |
| 4,527,709 | 7/1985 | Kondo et al. | 220/20.5 |
| 4,675,010 | 6/1987 | Siposs et al. | 604/319 |

Primary Examiner—Willis Little
Attorney, Agent, or Firm—Edward H. Loveman

[57] ABSTRACT

This container assembly is closed by removable cover and includes a base formed by two transparent nested cup shaped inner and outer members spaced to define a closed thermal insulation chamber therebetween. The inner member has a diametral partition structure dividing this member into two compartments. The cover has two spaced nipples to which may be connected respectively to an aspiration tube and a needle assembly for discharging fluids or a wash from a follicle or another similar site, into the chambers when the cover is rotated to either one of two positions on the base. The cover may be replaced by a transparent, imperforate cover for reviewing the contents of the compartments by a microscope to detect the presence of an oocyte.

11 Claims, 3 Drawing Sheets

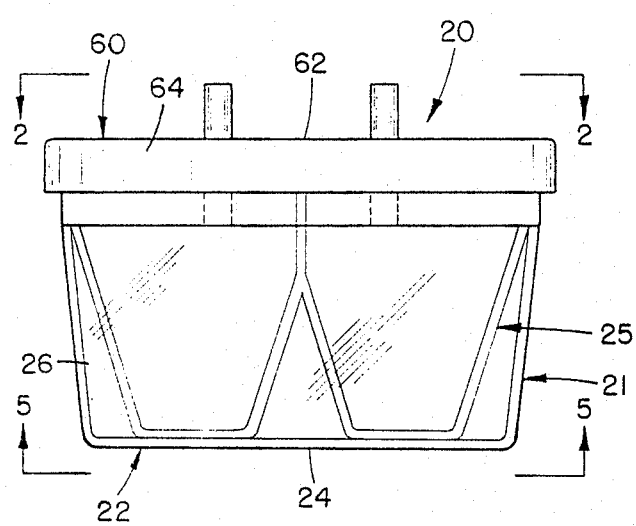
FIG.1
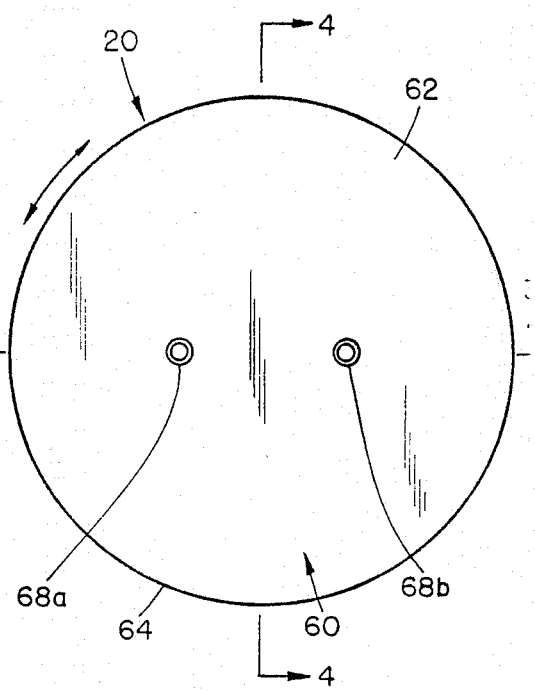
FIG.2
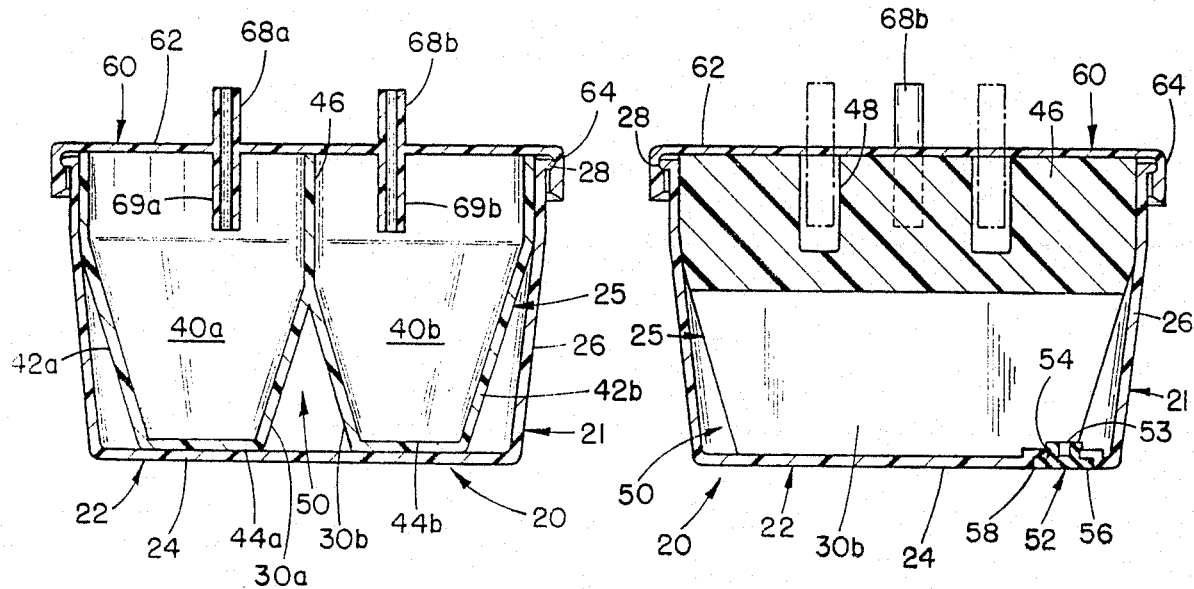
FIG.3
FIG.4

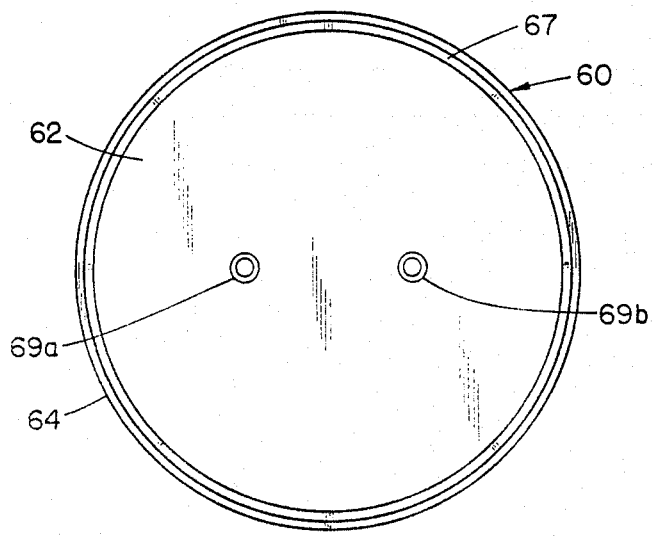
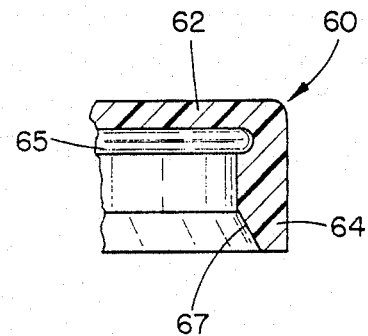
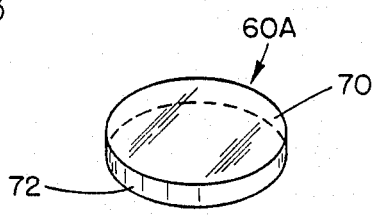
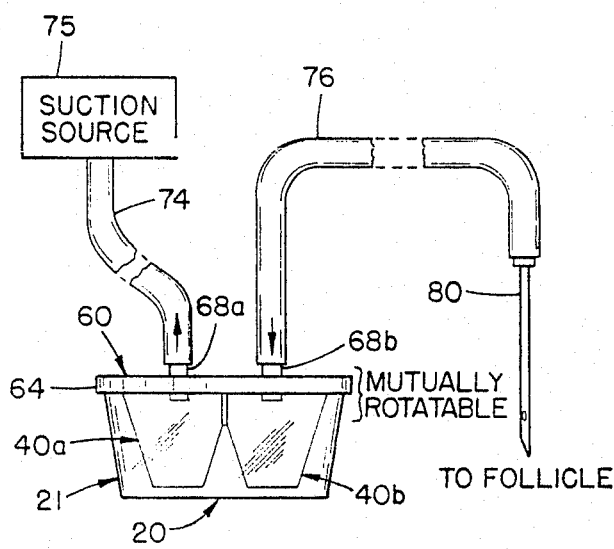
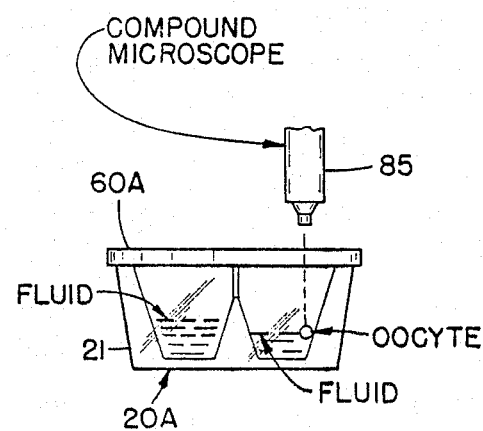

ASPIRATION CONTAINER ASSEMBLY FOR COLLECTING FOLLICULAR FLUIDS

BACKGROUND OF THE INVENTION

1. Field of the Invention

This invention relates to the art of devices used in performing in vitro fertilization procedures, especially devices for receiving and collecting oocytes, ova or eggs, and fluids aspirted from an ovary of a patient; and more particularly, the invention concerns a novel container for receiving and collecting such oocytes and fluids, and for retaining the same while they are being examined under a microscope.

2. Description of the Prior Art

The conventional procedure for obtaining oocytes and fluids from an ovary of an anesthetized patient, generally involves the puncture by a surgeon of an immobilized ovary. Then under microscopic observation a follicle is punctured by a hollow needle and follicular fluid is drawn out via an aspiration tube under suction. This fluid is discharged into a flask, test tube, or trap which is conveyed to an inspection station where the contents of the trap are emptied into a petri dish or other vessel for microscopic examination to determine the presence of an oocyte or oocytes. Immediately after the follicular fluid is removed another trap is provided to receive a media used to rinse the follicle, needle, and aspiration tube. This trap is then conveyed to the inspection station where the contents of the trap are emptied into another vessel for microscopic examination of the media. Generally, approximately 70% to 80% of the oocytes are found in the original aspirant, and 20% to 30% of the oocytes are found in the follicular wash. At least two collection traps are required per aspiration, one follicular fluid and one for the follicular wash. Generally more than one wash of a follicle is necessary in order to insure succession in obtaining to collect the oocyte. This prior procedure for collecting and examining the follicular fluid and follicular wash has several drawbacks and disadvantages. In the first place it is very laborious, since at least two washes must be used for each aspiration, and there may be as many as five to seven follicles found in each of two human ovaries during the procedure. Thus, many viewing dishes or vessels are required for microscopic examinations, one for each follicle aspirated and one for each aspirated wash. The emptying of the contents of the traps into viewing dishes makes it difficult or impossible to retain the fluid contents under stable, optimum temperature conditions, and the exposure to ambient air of the fluid contents of the traps is most undesirable. Some traps such as test tubes must be held manually or if placed in a stand, are not mechanically stable, and can tip over during the aspiration process. Also, several skilled attendants are required to assist the surgeon and to handle the traps containing the aspirated fluids.

SUMMARY OF THE INVENTION

It is a principal object of the invention to avoid the difficulties and disadvantages encountered in performing the follicular aspirations and subsequent microscopic examinations referred to above, by providing a novel container assembly having a base closed by a removable cover. The base is formed by nesting, integrally joined, transparent inner and outer cup shaped members. A closed space is defined between the cup shaped members to define a thermal insulation chamber. The inner member has a diametral partition structure dividing this member into two compartments which individually and separately receive the follicular fluid and follicular wash fluid under suction. The contents of the compartments are maintained under stable, optimum temperature conditions by the closed thermal insulation chamber. The cover is provided with a pair of spaced nipples to one of which a suction tube can be connected. A tube may be connected between the other nipple and a hollow needle assembly used to pierce a follicle being aspirated. After the follicular fluid is discharged into one compartment of the container, the cover may be rapidly rotated 180 degrees to discharge the follicular wash fluid into the other chamber. Multiple follecular rinses may be collected in each chamber, thereby decreasing the number of collection vessels per follicule. This rotatable cover can be rapidly interchanged with a flat transparent cover for viewing the contents of the two chambers under a microscope. This new aspiration container assembly materially reduces the time of surgery and the time during which the patient is under anesthesia, since the follicular aspirations may be performed more rapidly. Another advantage is the reduction in the number of personnel and amount of equipment required to perform the follicular fluid collection procedure. Also the exposure of the aspirated follicular fluids to ambient air and consequent environmental contamination is minimized or avoided altogether, since the aspirated fluids need not be transferred to individual viewing vessels. The covered container serves as the viewing vessel for microscopic examination purposes. Furthermore the contents of the container including the oocytes and the follicular fluids are maintained under stable temperature conditions at all times during collection and microscopic examination.

These and other objects and many of the attendant advantages of this invention will be readily appreciated as the same becomes better understood by reference to the following detailed description when considered in connection with the accompanying drawings in which:

BRIEF DESCRIPTION OF THE DRAWINGS

FIG. 1 is a side elevational view of an aspiration container embodying the invention;

FIG. 2 is a reduced top plan view of the container of FIG. 1 taken along line 2—2 of FIG. 1;

FIG. 3 is a vertical sectional view taken along line 3—3 of FIG. 2;

FIG. 4 is a vertical sectional view taken along line 4—4 of FIG. 2, 90 degrees to the view of FIG. 3;

FIG. 8 is a reduced bottom plan view of the cover per se;

FIG. 9 is an enlarged fragmentary sectional view of the cover taken along line 9—9 of FIG. 7;

FIG. 10 is a reduced perspective view of an imperforate transparent cover interchangeable with the cover shown in FIGS. 1-4, and 7-9; and FIGS. 11 and 12 are schematic diagrams employed in explaining the mode of use and operation of the invention.

DESCRIPTION OF THE PREFERRED EMBODIMENTS

Figure 5:
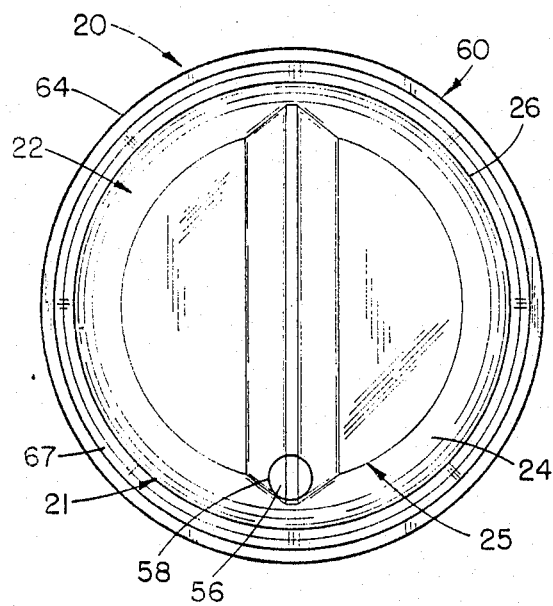
FIG. 5 is a reduced bottom plan view of the container taken along line 5—5 of FIG. 1.
Figure 6:
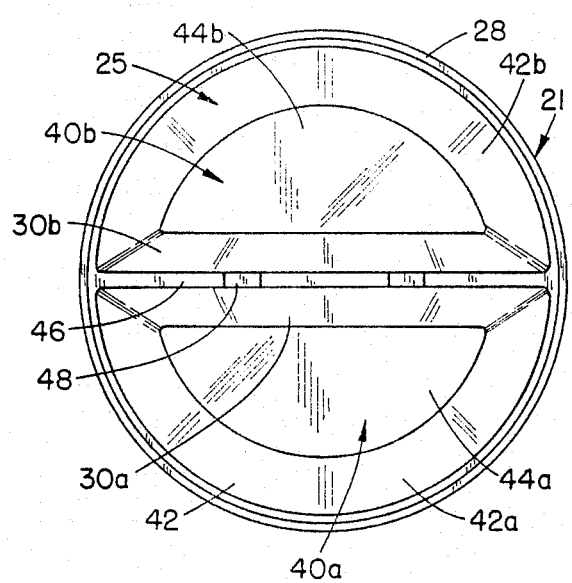
FIG. 6 is a top plan view of the container of FIGS. 1, 2, 3, with the cover removed.
Figure 7:
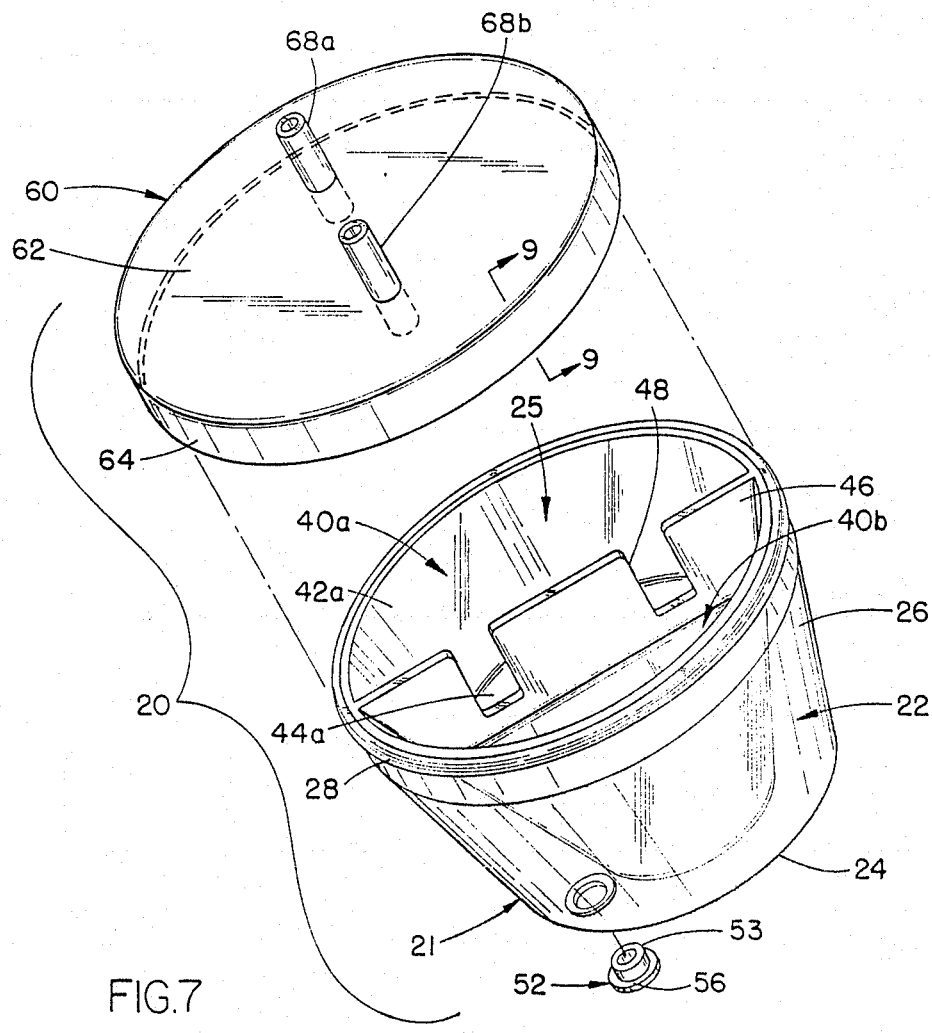
FIG. 7 is an exploded perspective view of parts of the container.

Referring now to the drawings wherein like reference characters designate like or corresponding parts throughout, there is illustrated in FIGS. 1-5 and 7 an aspiration container assembly 20 embodying the invention. The container assembly 20 has a conical base 21 formed by inner and outer nested, transparent, plastic cups or cup shaped members 22, 25. The outer cup 22 is formed with a flat circular bottom wall 24 and an integral frustoconical side wall 26 which flares outwardly to a wider top having a circumferential outer bead or ridge 28. Nested inside the cup 22 and integrally joined to the cup 22 at the top is the cup shaped member 25 which has a diametral partition structure including two flat, flaring, inclined, bifurcated walls 30a, 30b dividing the member 25 into two compartments 40a, 40b. The member 25 has outer curved semiconical side walls 42a, 42b and flat semicircular bottom walls 44a, 44b; see FIG. 6. The flat, inclined partition walls 30a, 30b are integral with flat, diametral, vertical, upper partition wall portion 46 formed with two rectangular spaced notches 48. The inner cup 25 is integrally joined to the outer cup 22 at the upper ends of the cups; see FIGS. 6, 7. Inside the cup 22 is a closed chamber 50 surrounding the compartments 40a, 40b. A rubber plug 52 has a cylindrical stem 53 inserted in a hole 54 in the bottom wall 24 of the outer cup 22. The plug 52 has a large round head 56 seated in a recess 58 hermetically sealing the chamber 50. The chamber 50 defines a dead air space which may be filled with air or other gas or a liquid. Alternatively, a vacuum may be drawn in the chamber 50 to define a thermal insulating space all around the compartments 40a and 40b.

A cap or cover 60 is provided for the base 21. The cover 60 has a circular top wall 62 and a circumferential annular skirt or rim 64, provided with an internal groove 65 to engage the bead 28; see FIG. 9. The cover 60 has an internal beveled edge 67 to facilitate engaging the cover 60 on the base 21. Once mounted, the cover 60 may be rotated with respect to the base 21. The cover 60 is formed with two integral spaced nipples 68a, 68b extending upwardly from the wall 62; see FIGS. 7, 8. The nipples 68a, 68b have lower aligned sections 69a, 69b extending downwardly into the compartments 40a and 40b depending on the rotational position of the cover 60. FIG. 3 shows the nipple section 69a extending downwardly into the compartment 40a and the nipple section 69b extending downwardly into the compartment 40b. It will be apparent that the cover 60 may be rotated 180 degrees on the base 21 so that the nipple sections 69a, 69b clear the ridge 46 by passing through the notches 48 as indicated by dotted lines in FIG. 4. This will position the nipple section 69a in the compartment 40b and the nipple section 69b in the compartment 40a. The cups 22 and 25 of the base 21 are made of transparent plastic material. The cover 60 may be made of transparent or opaque plastic. The entire container assembly 20 is light in weight, inexpensive to manufacture, and can be discarded after a single use. To complete the assembly there is provided another cover 60A without nipples. This cover is interchangeable with the cover 60; see FIG. 10. The cover 60A has an imperforate circular top wall 70 and an integral depending cylindrical, circumferential wall or skirt 72 which engages on the wider top open end of the base 21. The functions of covers 60 and 60A and the base 21 will now be explained with reference to FIGS. 11 and 12.

As shown in FIG. 11, a flexible suction tube 74 may be connected between one nipple 68a and a source 75 of suction. Another flexible aspiration tube 76 may be connected between the other nipple 68b and a hollow needle 80 used to pierce a follicle in an ovary. When the suction is applied the fluid contents of the follicle will be drained via the needle 80 into the compartment 40b in the base 21. Then the cap 60 will be rotated 180 degrees on the base 21, while the follicle in the ovary is washed along with the interior of the tube 76 and the needle 80. The follicular wash fluid is drained into the compartment 40a. Then the cap 60 is removed and is immediately replaced by the transparent cap 60A as shown in FIGS. 10 and 12. There may be an oocyte in either compartment 40a and 40b. To find it, the container 20A is placed under a compound microscope 85. The contents of the compartments 40a, 40b and particularly their inclined inner side walls 30a, 30b and inclined outer walls 42a, 42b which provide increased viewability, are carefully scanned since the desired oocyte may be in either compartment or both. In many cases, the washing of the follicle, the tube 76 and the needle 80 is repeated with the wash fluid collected in a second container 20A. It will be noted that the compartments remain closed at all times except during the very short time it takes to interchange covers 60 and 60A, so that the contents of the container are protected from outside ambient conditions. The container base 21 may be preheated or chilled to any desired temperature before the container is put in use. Chamber 50 containing air, liquid, or a vacuum provides an effective stable thermal insulation, to keep the contents of the containers 20 and 20A at a predetermined temperature. Thereafter, the closed container 20A can be taken away for further processing. Once the oocyte has been located and identified in either the follicular fluid in one compartment of the container or in the follicular wash fluid in the other compartment, the oocyte can be quickly collected and placed in an appropriate incubation medium for continuation of the in vitro fertilization procedure.

Among the advantages obtained from use of the containers 20 and 20A as described are the following:

1. The time required for collecting oocytes is minimized.

2 The shorter time for collection, reduces the time during the patient is anesthetized.

3. The aspiration container allows easy handling of aspirated oocyte.

4. Transport of the container is easier, and the chance of spillage is practically eliminated.

5. Speed in examination and identification of oocyte in the container is enhanced, thus reducing the time that the oocyte is exposed to non-physiological environments.

6. Since the oocyte collection and examination procedure is simplified and speeded up, it becomes possible to reduce the number of personnel involved in the procedure; so that savings of labor and effort are achieved, and changes of human errors occurring are reduced.

7. The containers can be pre-sterilized and delivered to the operating room in sterile condition, so further sterilization is rendered unnecessary.

8. The containers can be supplied with chambers 50 under vacuum, so that the thermal insulation feature is already built into the containers.

9. The quick turn around of cap 60 to collect the follicular wash fluid is an especially important advantage in speeding up the oocyte collection process. Furthermore, once the follicule is punctured, blood starts to accumulate in the follicular fluid, hence, it is crucial that the follecule be aspirated and washed, the appropriate number of times, as rapidly as possible. Since this novel and unique collection vessel permits rapid collection of both the follicular fluid as well as wash fluid, the quantity of blood in the fluids collected with this vessel is minimum.

10. The use of the transparent cover 60A makes it possible to eliminate the prior transfer of contents of the aspiration container to a viewing vessel, and thus, helps to reduce the cost of the procedure.

It should be understood that the foregoing relates to only a preferred embodiment of the invention, which has been by way of example only, and that it is intended to cover all changes and modifications of the examples of the invention herein chosen for the purpose of the disclosure, which do not constitute departures from the spirit and scope of the invention.

What is claimed is:

1. An aspiration container assembly for follicular fluids, comprising:
   a base having nested integrally joined outer and inner cup shaped members defining a closed thermal insulation chamber therebetween;
   said inner cup shaped member having an inner partition structure integral with a plurality of walls defining two compartments in said inner member for receiving said fluids; and a cover rotatably and removably mounted on said base for closing said compartments;
   said cover having first tube engagement means thereon for attaching a suction tube thereto for applying suction to the interior of said inner cup shaped member;
   said cover having second tube engagement means thereon for attaching a fluid aspiration tube thereto;
   both of said tube engagement means opening into said inner cup shaped member, and being spaced apart so that said fluid conduction tube discharges said fluids into one of said two compartments when said cover is in one position of rotation on said base, and so that said fluid aspiration tube discharges said fluids into the other one of said two compartments when said cover is rotated to another position on said base, while suction is applied to said fluid aspiration tube via said compartments and said suction tube.

2. An aspiration container assembly as defined in claim 1, wherein said inner and outer cup shaped members are made of transparent material; and further comprising a transparent other cover interchangeable with said first named cover on said base, and removably mountable on said base for microscopic examination of said fluids in said compartments.

3. An aspiration container assembly as defined in claim 1, wherein said outer cup shaped member has an opening communicating with said chamber, and a plug removable engaged in said opening for selectively retaining liquid, air or vacuum in said chamber to insulate thermally said compartments from external ambient temperature conditions.

4. An aspiration contained assembly as defined in claim 2, wherein certain ones of said inner cup shaped member are curved to define outer sides of said compartments, and wherein said partition structure comprises a flat portion and two integral bifurcated flat other positions defining inner sides of said compartments.

5. An aspiration container assembly as defined in claim 4, wherein said certain curved walls and said flat other portions of said partition structure are so inclined with respect to said transparent other cover as to maximize viewability by a microscope of any oocytes collected in said compartments.

6. An aspiration container assembly as defined in claim 1, wherein said first and second tube engagement means are nipples spaced apart diametrally of said cover and extending upwardly therefrom for attachment of said tubes thereto.

7. An aspiration container assembly as defined in claim 6, wherein said cover further comprises nipple sections respectively axially aligned with said nipples and extending downwardly into said inner cup shaped member, said partition structure comprising a flat portion extending diametrally of said inner cup shaped member and having spaced notches to clear said nipple sections when said cover is rotated.

8. An aspiration container assembly as defined in claim 7, wherein said inner and outer cup shaped members are made of transparent material; and further comprising a transparent other cover interchangeable with said first named cover on said base, and removably mountable on said base for microscopic examination of said fluids in said compartments.

9. An aspiration container assembly as defined in claim 8, wherein said partition structure further comprises two integral bifurcated flat other portions defining inner sides of said compartments, and wherein certain walls of said inner cup shaped member are curved to define outer sides of said compartments.

10. An aspiration container assembly as defined in claim 9, wherein said flat other portions of said partition structure and said certain walls are so inclined with respect to said transparent other cover as to maximize viewability by a microscope of any oocytes collected in said compartments.

11. An aspiration container as defined in claim 10, wherein said outer cup shaped member has an opening communicating with said chamber, and a plug removably engaged in said opening for selectively retaining liquid, air or vacuum in said chamber to insulate thermally said compartments from external ambient temperature conditions.

* * * * *